United States Patent [19]

Miller et al.

[11] 4,044,098

[45] Aug. 23, 1977

[54] REMOVAL OF MERCURY FROM GAS STREAMS USING HYDROGEN SULFIDE AND AMINES

[75] Inventors: Alvin J. Miller; William F. Tuckett, both of Bartlesville, Okla.

[73] Assignee: Phillips Petroleum Company, Bartlesville, Okla.

[21] Appl. No.: 687,476

[22] Filed: May 18, 1976

[51] Int. Cl.$^2$ .................. B01D 47/00; B01J 8/00; C01B 17/20
[52] U.S. Cl. .................. 423/210; 423/561 B; 55/72
[58] Field of Search .................. 423/88, 210, 215.5, 423/228, 229, 561 B; 55/72

[56] References Cited

U.S. PATENT DOCUMENTS

| | | | |
|---|---|---|---|
| 3,194,629 | 7/1965 | Dreibelbis et al. | 23/2 |
| 3,661,509 | 5/1972 | Ferrara et al. | 23/2 S |
| 3,718,457 | 2/1973 | Entwise et al. | 423/561 B |
| 3,786,619 | 1/1974 | Melkersson et al. | 423/210 |
| 3,826,819 | 7/1974 | Orlandini et al. | 423/561 B |
| 3,849,537 | 11/1974 | Allgulin | 423/210 |
| 3,855,387 | 12/1974 | Brockmiller et al. | 423/210 |
| 3,919,389 | 11/1975 | Jonescu | 423/210 |
| 3,932,149 | 1/1976 | Melkersson | 423/210 |
| 3,954,451 | 5/1976 | Kinoshita | 423/210 |
| 3,961,031 | 6/1976 | Yasui et al. | 423/561 B |

OTHER PUBLICATIONS

Gas Purification, Kohl et al., pp. 22 & 25, 1960.
Oil & Gas, 64, 10/24/1966, pp. 110–118.

*Primary Examiner*—O. R. Vertiz
*Assistant Examiner*—Eugene T. Wheelock

[57] ABSTRACT

A process is provided in which a gas, particularly a sulfur-free natural gas, that contains mercury is contacted with an amount of hydrogen sulfide in excess of the stoichiometric amount of hydrogen sulfide necessary to precipitate sulfides of mercury with further contact with an amine that is an absorption agent for hydrogen sulfide. Hydrogen sulfide precipitates sulfides of mercury from the gas stream while the amine absorbs the excess hydrogen sulfide to produce a gas stream of minimal sulfur content with a reduced mercury content that can be below the range of detection.

9 Claims, 1 Drawing Figure

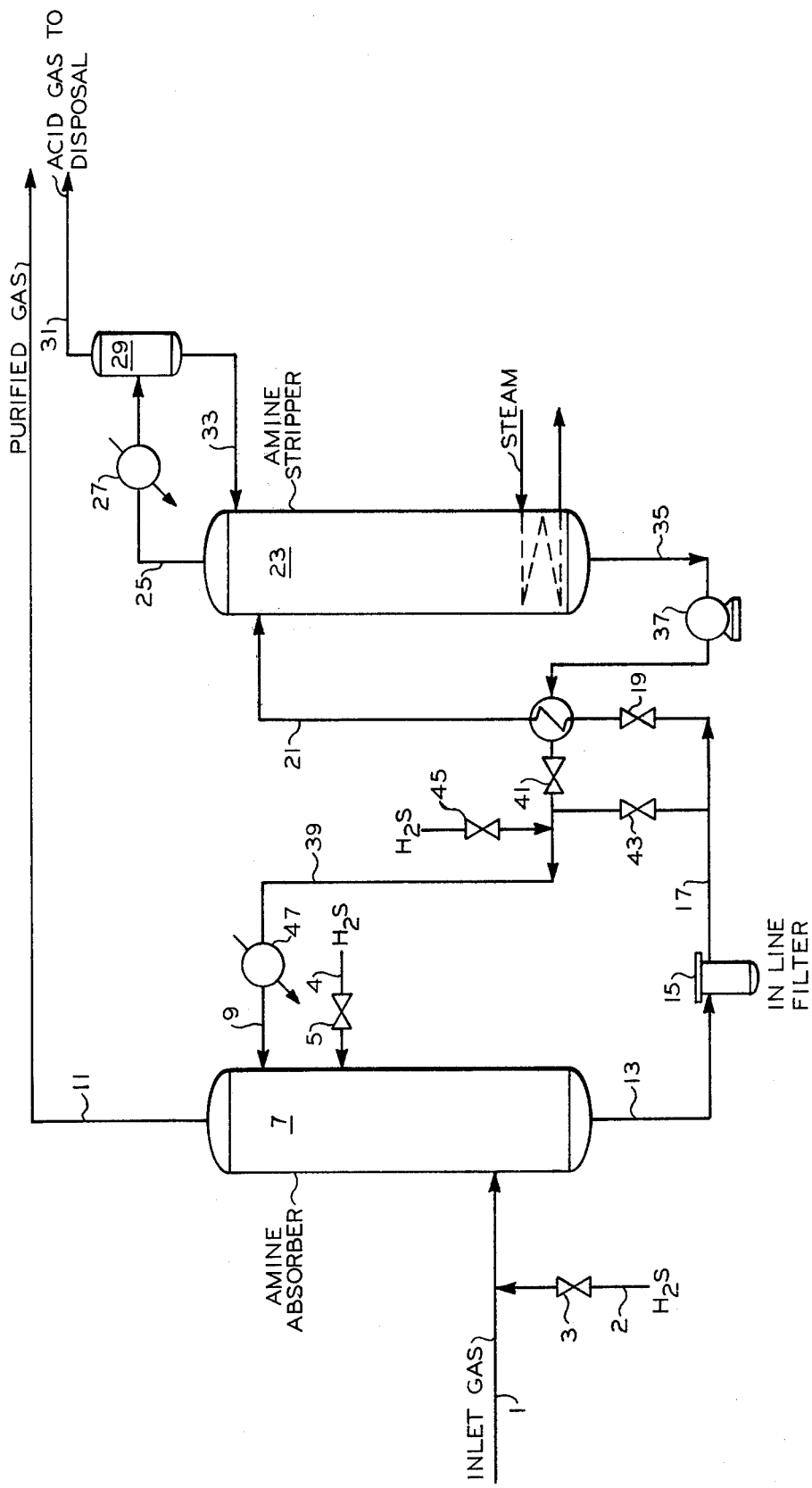

REMOVAL OF MERCURY FROM GAS STREAMS USING HYDROGEN SULFIDE AND AMINES

BACKGROUND OF THE INVENTION

This invention relates to the purification of gas streams. In one of its aspects this invention relates to the removal of small amounts of mercury from a sulfur-free natural gas. In another of its aspects this invention relates to the precipitation of mercury by contact with suitable sulfur-containing agents. In yet another of its aspects this invention relates to the absorption of hydrogen sulfide using an amine absorption agent. In its basic concept this invention relates to an integrated process for treating a gas stream with a precipitating agent to remove mercury and further treating the gas stream with an absorption agent to control the amount of precipitating agent left in the gas stream.

Most raw natural gas contains hydrogen sulfide in concentrations varying from a few parts per million to 20 mole percent or more. This sulfur content is the result of natural gas deposits being associated with sulfur or sulfur-containing minerals or with the natural gas being formed in the presence of sulfur-containing organic matter. Sulfur-containing natural gas does not contain mercury because mercury that had been present in the reservoir would have been converted to a nonvolatile sulfide.

There are, however, some natural gas deposits that are sulfur-free. In recent years it has been discovered that many sulfur-free natural gas deposits contain small amounts of mercury, usually in the range of about 1 part per million or less. The presence of even this small amount of mercury poses a potential health hazard under some circumstances. There is, also, an ever-present potential safety hazard in using this gas in cryogenic processing plants where the mercury can amalgamate with aluminum in processing equipment eventually weakening the metal and leading to a leakage or rupture.

It has now been discovered that mercury can be removed essentially quantitatively by injecting at least a stoichiometric amount of hydrogen sulfide into a natural gas stream to precipitate sulfides of mercury. Since from a practical standpoint it is necessary to inject an excess of hydrogen sulfide into the gas stream over that which will stoichiometrically combine with the mercury, further treatment of the natural gas stream is necessary both for controlling the sulfur content of the treated gas and to remove the precipitated sulfides of mercury.

It is therefore an object of this invention to provide a process for treating gas streams to lower the mercury content of the gas. It is also an object of this invention to provide a treated gas stream from which mercury has been removed by treatment with hydrogen sulfide and which contains a minimal amount of sulfur treating agent. It is a further object of this invention to provide a process by which mercury can be removed from a natural gas stream by treating with hydrogen sulfide with the retention of a minimal amount of hydrogen sulfide in the natural gas stream.

Other aspects, concepts, objects and the various advantages of this invention will become apparent upon reading the specification and the appended claims.

STATMENT OF THE INVENTION

In accordance with this invention a process for treating a natural gas stream containing mercury is provided to produce natural gas with a reduced mercury content. The process entails contacting the mercury-containing natural gas stream with an amount of hydrogen sulfide sufficient to cause precipitation of mercury as mercury sulfides and the contacting of the natural gas stream in the presence of the hydrogen sulfide with an amine that will absorb hydrogen sulfide to absorb hydrogen sulfide in excess of the mercury precipitating amount. The precipitated sulfides of mercury are mechanically removed. The merrcury content of the natural gas stream can be reduced below the minimum detectable, about 1 part per billion, and the hydrogen sulfide content of the treated gas can be maintained at less than about 0.5 parts per million using this process. Although this invention arose in the treatment of natural gas streams, and is herein so described, it will be apparent to those skilled in the art that the process is applicable to the treatment of any gaseous stream containing mercury.

In one embodiment of this invention a natural gas stream containing mercury is contacted with an amount of hydrogen sulfide in excess of the stoichiometric amount of hydrogen sulfide necessary to precipitate sulfides of mercury so that a natural gas containing hydrogen sulfide is produced. This mixture is then treated by contacting with a liquid amine that will absorb hydrogen sulfide so that the hydrogen sulfide content in the natural gas stream is reduced and the precipitated sulfides of mercury are scrubbed from the natural gas stream.

For greater efficiency this embodiment can have integrated with it a conventional stripping operation for removing hydrogen sulfide from the amine absorbing agent after contact with the natural gas. The stripped absorbent is then recycled for absorbing contact with natural gas stream.

In another embodiment of the invention the mercury-containing natural gas stream can be contacted with a liquid amine in which there is absorbed an amount of hydrogen sulfide sufficient to precipitate the mercury contained in the natural gas. In this embodiment a sufficient amount of the amine absorbent is circulated to carry hydrogen sulfide in excess of that required to form sulfides of mercury upon contact with the mercury. The sulfides of mercury are mechanically removed from the absorber liquid stream after contact with the natural gas. Hydrogen sulfide is added to the absorber stream as necessary to maintain the required level for removal of the mercury.

Although, theoretically, only the stoichiometric amount of hydrogen sulfide necessary to combine with the mercury to produce sulfides of mercury is required to carry out the reaction; from a practical standpoint a higher hydrogen sulfide content is ncessary. To assure that all the mercury is converted to sulfides and to provide a significant concentration of hydrogen sulfide in the rich amine system to insure that mercury is maintained in the sulfide state in the amine system, it is preferable to add at least a 200 percent excess of hydrogen sulfide, or an amount that theoretically provides at least 5 parts per million hydrogen sulfide in the gas stream, whichever is larger.

Since hydrogen sulfide is never completely stripped from amine solutions in commercial operations it is also a practical expedient to control the level of hydrogen sulfide in the absorbant circulating to be contacted with the natural gas at a lvel in the range of about 5 to about 10 grains per gallon of solution (0.85–1.71 gm/l). When the hydrogen sulfide is added directly to the absorbent for circulation to be contacted with a natural gas the level of hydrogen sulfide content in the absorbent is held at at least the 200 percent excess of hydrogen sulfide or the amount of hydrogen sulfide that would amount to 5 parts per million in the natural gas.

Although any absorbent for hydrogen sulfide that can efficiently maintain the desired level of hydrogen sulfide content in the treated natural gas would be useful in this invention, the use of amines for the absorption of hydrogen sulfide is preferred. Some of the amine absorbents that are particularly useful in this invention are aliphatic amines, particularly alkanol amines. Some readily available compounds are monoethanolamine, diethanolamine, and triethanolamine. Of these, monoethanolamine is particularly preferred because of its convenient use.

The removal of precipitated sulfides can be accomplished in any convenient known manner. A particularly simple and effective means is the installation of a cartridge type filter at a convenient point in the system. Such filters are frequently used in amine circulation systems to filter out small particles of solids such as mill scale, iron sulfide and the like.

The invention can best be understood by reference to the drawing which sets forth in one FIGURE alternative systems for contacting natural gas with hydrogen sulfide or an absorbent in which is maintained a desired level of hydrogen sulfide for treating natural gas.

Referring now to the drawing a natural gas stream containing mercury in introduced into line 1. Hydrogen sulfide is introduced through line 2 and valve 3 into line 1 or through line 4 and valve 5 into absorber 7 to be mixed with the natural gas providing hydrogen sulfide in excess of the stoichiometric amount for reaction with the mercury. In this contacting precipitates of sulfides of mercury are formed. The gaseous mixture from line 1 enters absorber 7 where it is contacted, preferably countercurrently, with an amine absorbent from line 9 which not only acts to absorb hydrogen sulfide, but also other acid gases such as carbon dioxide. In this contacting the precipitates are washed from the gas stream and the excess hydrogen sulfide is removed from the gas stream so that natural gas with a reduced mercury content and containing a minimal amount of hydrogen sulfide is removed from the absorber through line 11 as a purified gas stream.

With valve 43 closed the absorber liquid containing precipitated sulfides of mercury leaves the absorber through line 13, pass through an inline filter 15 where the precipitates are removed, and through line 17, valve 19 and line 21, into an absorbent stripping system 23 in which with conventional steam-stripping, an overhead comprising hydrogen sulfide an dother acid gases is discharged through line 25 which, after passing through cooler 27 and condensate collector 29, is discharged through line 31. Condensed absorbent is recycled to the stripper through line 33. From the base of the stripping column 23 stripped absorbent is passed through line 35 and pump 37 back to the absorber column 7 through valve 41, line 39, and optionally cooler 47.

In another embodiment of the invention with valves 5, 19 and 41 closed and valve 43 opened, inlet gas is passed through line 1 into the absorber column 7 where it is contacted with absorbing liquid containing hydrogen sulfide passed into the absorber through line 9. After contact, natural gas of reduced mercury content is discharged through line 11 and the absorbing liquid containing percipitated sulfides of mercury is passed through line 13 to in-line filter 15 for removal of the precipitates, then through line 17 and valve 43 to line 39 where makeup hydrogen sulfide is passed through valve 45 into line 39 to maintain the hydrogen sulfide content of the absorbing liquid which is passed through line 9 into the absorber.

The invention is illustrated in the following calculated example.

EXAMPLE I

A 10 MMSCFD (million standard cubic feet per day) (3.3 m³/s) natural gas stream essentially free of $H_2S$ contains 1 ppm Hg. Hydrogen sulfide is continuously blended into the gas to maintain a concentration of 5 ppm being fed to the amine absorber. This absorber, which is 7 feet (2.14 m) in diameter by 68 feet (20.8 m) high, contains 24 trays and is operated at 200 psig (1.48 MPa) and 100° F (38° C). An aqueous solution of 30 weight percent monoethanolamine is circulated through the absorber at a rate of 0.2 gallon/minute (0.000013 m³/s) to reduce the $H_2S$ content of the treated gas to less than 0.5 ppm and the mercury to below the detectable limit (~ 1 ppb) (parts per billion). The rich amine is conventionally stripped using a reboiler or live steam, cooled by heat exchange and recirculated to the absorber.

We claim:

1. A process for treating a gas stream that contains mercury thereby producing a gas stream with reduced mercury content and minimal sulfur content, said process comprising:
    a. contacing said mercury-containing gas stream with an amount of hydrogen sulfide in excess of the stoichiometric amount of hydrogen sulfide necessary to precipitate sulfides of mercury thereby producing a gas stream containing hydrogen sulfide; and
    b. treating said gas stream containing hydrogen sulfide by contact with an amine capable of absorbing hydrogen sulfide to reduce the hydrogen sulfide content of the gas stream and remove precipitated sulfides of mercury from said stream thereby producing a gas stream of reduced mercury content and a minimal sulfur content.

2. A process according to claim 1 wherein said amine containing precipitated mercury sulfides and hydrogen sulfide is
    a. filtered to remove precipitates;
    b. stripped to remove absorbed hydrogen sulfide; and
    c. recirculated to contact said gas stream.

3. A process according to claim 2 wherein said stripping is controlled to maintain an amount of hydrogen sulfide in the recycled amine in the range of about 5 to about 10 grains per gallon of solution.

4. A process according to claim 1 wherein said gas stream is a natural gas stream.

5. A process according to claim 4 wherein said amine is monoethanolamine.

6. A process for treating a gas stream that contains mercury thereby producing a gas stream with reduced mercury content and minimal sulfur content, said process comprising contacting said mercury-containing gas stream with an amine capable of absorbing hydrogen sulfide with the amine containing an amount of hydrogen sulfide sufficient to precipitate the mercury contained in the gas stream, said amine in an amount sufficient to retain hydrogen sulfide in excess of the amount required to precipitate said mercury.

7. A process according to claim 6 wherein said amine containing precipitated mercury sulfides is
   a. filtered to remove precipitates;
   b. has added thereto hydrogen sulfide in an amount to maintain the level of hydrogen sulfide within precipitation range; and
   c. with the added hydrogen sulfide is recycled to contact said gas stream.

8. A process according to claim 6 wherein said gas stream is a natural gas stream.

9. A process according to claim 8 wherein said amine is monoethanolamine.

* * * * *